United States Patent
Hamilton et al.

(10) Patent No.: US 10,066,271 B2
(45) Date of Patent: Sep. 4, 2018

(54) GENETIC LOCI ASSOCIATED WITH MAL DE RIO CUARTO VIRUS IN MAIZE

(71) Applicant: Agrigenetics, Inc., Indianapolis, IN (US)

(72) Inventors: Jennifer L. Hamilton, Indianapolis, IN (US); Juan P. Raimondi, Pergamino (AR); Trisha Borowicz, Greenfield, IN (US); Cherie Ochsenfeld, Brownsburg, IN (US); James W. Bing, Zionsville, IN (US)

(73) Assignee: AgriGenetics, Inc., Indianapolis, IN (US)

( * ) Notice: Subject to any disclaimer, the term of this patent is extended or adjusted under 35 U.S.C. 154(b) by 238 days.

(21) Appl. No.: 14/585,024

(22) Filed: Dec. 29, 2014

(65) Prior Publication Data

US 2015/0184254 A1    Jul. 2, 2015

Related U.S. Application Data

(60) Provisional application No. 61/920,855, filed on Dec. 26, 2013.

(51) Int. Cl.
*C12Q 1/68* (2006.01)
*A01H 5/10* (2006.01)
*A01H 1/02* (2006.01)
*A01H 1/04* (2006.01)
*C12Q 1/6895* (2018.01)

(52) U.S. Cl.
CPC .............. *C12Q 1/6895* (2013.01); *A01H 1/02* (2013.01); *A01H 1/04* (2013.01); *A01H 5/10* (2013.01); *C12Q 2600/13* (2013.01); *C12Q 2600/156* (2013.01)

(58) Field of Classification Search
None
See application file for complete search history.

(56) References Cited

PUBLICATIONS

Bonamico et al. (ΦYTON, (2010), 79: pp. 31-38).*
Maize Genetics and Genomics Database (www.maizegdb.org, accessed on Nov. 16, 2016).*
Collard et al. (Euphytica (2005) 142: 169-196)).*

* cited by examiner

*Primary Examiner* — Brent Page
*Assistant Examiner* — Jared Shapiro
(74) *Attorney, Agent, or Firm* — Magleby Cataxinos & Greenwood

(57) ABSTRACT

This invention relates to methods for identifying maize plants that having decreased MRCV. The methods use molecular markers to identify and to select plants with decreased MRCV or to identify and deselect plants with decreased MRCV. Maize plants generated by the methods of the invention are also a feature of the invention.

5 Claims, No Drawings

Specification includes a Sequence Listing.

GENETIC LOCI ASSOCIATED WITH MAL DE RIO CUARTO VIRUS IN MAIZE

CROSS-REFERENCE TO RELATED APPLICATION

This application claims the benefit of U.S. Provisional Patent Application Ser. No. 61/920,855, filed Dec. 26, 2013, the disclosure of which is hereby incorporated herein in its entirety by this reference.

TECHNICAL FIELD

The present invention relates to methods useful in decreasing Mal de Rio Cuarto Virus in maize plants.

BACKGROUND

Mal de Rio Cuarto Virus (MRCV) is considered to be the most prevalent and destructive viral disease of maize, *Zea mays* L., in Argentina. MRCV infection causes abnormal corn development and significantly reduces crop yield. The susceptible phenotype includes stunting, shortened internodes, cut and reduced leaves, deformed tassels with no anthers, reduced roots, underdeveloped ears with poor kernel sets and overall thickening of vascular tissues. The largest known outbreak of MRCV in Argentina to date occurred during the 1996/1997 growing season and affected nearly 300,000 hectares producing approximately $120 MM in yield losses. MRCV disease is vectored by the leafhopper *Delphacodes kuscheli*. Increased populations of *D. kuscheli* in 2006 apparently led to a reoccurrence of the viral disease in Argentinean corn plants, which significantly affected the 2007 harvest. Exploratory methods to control the disease using pesticides and other means of insect control have been unsuccessful and development of MCRV tolerant lines through selective breeding is a primary initiative for seed producers.

As *Bacillus thuringiensis* (Bt) technology becomes more widespread in Brazil and Northern Argentina, the amount of insecticide used on corn crops will most likely decrease. This reduction in insecticide may increase the numbers of leaf hoppers in the environment, thus amplifying MRCV disease pressure. Breeding resistance into corn is the principal and most effective control method to manage yield loss associated with MRCV disease. The development of molecular genetic markers has facilitated mapping and selection of agriculturally important traits in maize, and quantitative trait loci (QTL) for MRCV resistance have been identified. QTL conferring resistance to MRCV have been identified on chromosomes 1 and 8 (DiRenzo et al. 2004; Kreff et al. 2006), chromosome 2 (WO 2009/058335), and chromosomes 4 and 10 (Kreff et al. 2006). Introgression of QTL through the use of molecular markers associated with MRCV will increase the speed and accuracy of moving MRCV resistance into elite corn hybrids, thus improving the level of resistance in subtropical germplasm. Incorporating MRCV resistance into elite corn germplasm may prevent the spread of the viral disease to non-endemic regions.

Despite the fact that information for MRCV resistance QTL is available in the art, few pedigrees can be classified as highly tolerant and there is little evidence of any strong resistance to MRCV in commercially available hybrids. The is still a need for commercially acceptable hybrids that are MRCV resistant and for a method to develop and track resistant maize inbreds and hybrids through marker assisted breeding.

Described within is a method to map MRCV resistance QTL in a DH population using a bi-parental QTL mapping approach. The present invention allows selection of progeny which contain the genomic background of the agronomically desirable parent and the genomic trait of the MRCV resistant donor parent. The present invention also allows tracking of MRCV resistance QTL in order to introgress the MRCV resistance trait into new plants through traditional breeding.

BRIEF SUMMARY

In one embodiment, methods of identifying a maize plant that displays decreased MRCV, comprising detecting in germplasm of the maize plant at least one allele of a marker locus are provided. The marker locus is located within a chromosomal interval comprising and flanked by PZD00030.2 and DAS-PZ-7622; and at least one allele is associated with decreased MRCV. The marker locus can be selected from any of the following marker loci PZD00030.2, PZA02194-1, PZE-104104856, Mo17-14216, DAS-PZ-19059, PZE-104109680, PZE-104110452, PZB01461.2, DAS-PZ-4588, MAGI_38007, DAS-PZ-12232, MAGI_75461, PZA02614.2, chr4_206864219, KG-2634304, DAS-PZ-9024, DAS-PZ-11829, PZE-104135467, PZE-104136149, MAGI_73697, PZE-104137851, DAS-PZ-236, DAS-PZ-7082, MAGI_35446, DAS-PZ-12609, and DAS-PZ-7622, as well as any other marker that is linked to these markers. The marker locus can be found on chromosome 4, within the interval comprising and flanked by DAS-PZ-4588 and MAGI 75461, and comprises at least one allele that is associated with decreased MRCV. In some embodiments, the maize plant belongs to the Non-Stiff Stalk heterotic group. Maize plants identified by this method are also of interest.

In another embodiment, methods of identifying a maize plant that displays decreased MRCV, comprising detecting in germplasm of the maize plant at least one allele of a marker locus are provided. The marker locus is located within a chromosomal interval comprising and flanked by DAS-PZ-8199 and MAGI_105022-2; and at least one allele is associated with decreased MRCV. The marker locus can be selected from any of the following marker loci DAS-PZ-8199, Mo17-11151, PZB02059.2, PZE-105084059, DAS-PZ-20613, PZA01608-1, DAS-PZ-10982, PZE-105106594, DAS-PZ-15377, and MAGI_105022-2, as well as any other marker that is linked to these markers. The marker locus can be found on chromosome 5, within the interval comprising and flanked by PZB02059.2 and PZA01608-1, and comprises at least one allele that is associated with decreased MRCV. In some embodiments, the maize plant belongs to the Non-Stiff Stalk heterotic group. Maize plants identified by this method are also of interest.

In yet another embodiment, methods of identifying a maize plant that displays decreased MRCV, comprising detecting in germplasm of the maize plant at least one allele of a marker locus are provided. The marker locus is located within a chromosomal interval comprising and flanked by PZE-105159825 and PZE-105169090; and at least one allele is associated with decreased MRCV. The marker locus can be selected from any of the following marker loci PZE-105159825, PZE-105160788, PZA00545.26, PZA02015-11, PZA03167.5, PZE-105166278, and PZE-105169090, as well as any other marker that is linked to these markers. The marker locus can be found on chromosome 5, within the interval comprising and flanked by PZA00545.26 and PZE-105166278, and comprises at least one allele that is associated with decreased MRCV. In some embodiments, the maize plant belongs to the Non-Stiff Stalk heterotic group. Maize plants identified by this method are also of interest.

In another embodiment, method for identifying maize plants with decreased MRCV by detecting a haplotype in the germplasm of the maize plant are provided. The haplotype comprises alleles at one or more marker loci, wherein the one or more marker loci are found on chromosome 4 within the interval comprising and, flanked by, DAS-PZ-4588 and MAGI 75461. The haplotype comprises alleles at one or more marker loci, wherein the one or more marker loci are found on chromosome 4 and are selected from the group consisting of DAS-PZ-4588, MAGI 38007, DAS-PZ-12232, and MAGI_75461. The haplotype is associated with decreased MRCV.

In another embodiment, method for identifying maize plants with decreased MRCV by detecting a haplotype in the germplasm of the maize plant are provided. The haplotype comprises alleles at one or more marker loci, wherein the one or more marker loci are found on chromosome 5 within the interval comprising and, flanked by, PZB02059.2 and PZA01608-1. The haplotype comprises alleles at one or more marker loci, wherein the one or more marker loci are found on chromosome 5 and are selected from the group consisting of PZB02059.2, PZE-105084059, DAS-PZ-20613, and PZA01608-1. The haplotype is associated with decreased MRCV.

In another embodiment, method for identifying maize plants with decreased MRCV by detecting a haplotype in the germplasm of the maize plant are provided. The haplotype comprises alleles at one or more marker loci, wherein the one or more marker loci are found on chromosome 5 within the interval comprising and, flanked by, PZA02015-11 and PZE-105166278. The haplotype comprises alleles at one or more marker loci, wherein the one or more marker loci are found on chromosome 5 and are selected from the group consisting of PZA02015-11, PZA03167.5, and PZE-105166278. The haplotype is associated with decreased MRCV.

In a further embodiment, methods of selecting plants with decreased MRCV are provided. In one aspect, a first maize plant is obtained that has at least one allele of a marker locus wherein the allele is associated with decreased MRCV. The marker locus can be found on chromosome 4, within the interval comprising and flanked by PZD00030.2 and DAS-PZ-7622. The first maize plant can be crossed to a second maize plant, and the progeny resulting from the cross can be evaluated for the allele of the first maize plant. Progeny plants that possess the allele from the first maize plant can be selected as having decreased MRCV. Maize plants selected by this method are also of interest.

In another embodiment, methods of selecting plants with decreased MRCV are provided. In one aspect, a first maize plant is obtained that has at least one allele of a marker locus wherein the allele is associated with decreased MRCV. The marker locus can be found on chromosome 5, within the interval comprising and flanked by DAS-PZ-8199 and MAGI_105022-2. The first maize plant can be crossed to a second maize plant, and the progeny resulting from the cross can be evaluated for the allele of the first maize plant. Progeny plants that possess the allele from the first maize plant can be selected as having decreased MRCV. Maize plants selected by this method are also of interest.

In yet a further embodiment, methods of selecting plants with decreased MRCV are provided. In one aspect, a first maize plant is obtained that has at least one allele of a marker locus wherein the allele is associated with decreased MRCV. The marker locus can be found on chromosome 5, within the interval comprising and flanked by PZE-105159825 and PZE-105169090. The first maize plant can be crossed to a second maize plant, and the progeny resulting from the cross can be evaluated for the allele of the first maize plant. Progeny plants that possess the allele from the first maize plant can be selected as having decreased MRCV. Maize plants selected by this method are also of interest.

BRIEF DESCRIPTION OF FIGURES AND SEQUENCE LISTINGS

The invention can be more fully understood from the following detailed description and the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984) which are herein incorporated by reference in their entirety. The symbols and format used for nucleotide and amino acid sequence data comply with the rules set forth in 37 C.F.R. §1.822.

SEQ ID NOs:1-26 contain the SNPs and flanking sequences for markers linked to the chromosome 4 QTL.

SEQ ID NOs:27-33 contain the SNPs and flanking sequences for markers linked to the chromosome 5 QTL, which is defined by PZE-105159825 and PZE-105169090.

SEQ ID NOs: 34-43 contain the SNPs and flanking sequences for the markers linked to the chromosome 5 QTL, which is defined by DAS-PZ-8199 and MAGI_105022-2.

DETAILED DESCRIPTION

The present invention provides methods for identifying and selecting maize plants with decreased MRCV. The following definitions are provided as an aid to understand the invention.

Tailor Definitions

The term "allele" refers to one of two or more different nucleotide sequences that occur at a specific locus.

An "amplicon" is amplified nucleic acid, e.g., a nucleic acid that is produced by amplifying a template nucleic acid by any available amplification method (e.g., PCR, LCR, transcription, or the like).

The term "amplifying" in the context of nucleic acid amplification is any process whereby additional copies of a selected nucleic acid for a transcribed form thereof are produced. Typical amplification methods include various polymerase based replication methods, including the polymerase chain reaction (PCR), ligase mediated methods such as the ligase chain reaction (LCR) and RNA polymerase based amplification (e.g., by transcription) methods.

The term "assemble" applies to BACs and their propensities for coming together to form contiguous stretches of DNA. A BAC "assembles" to a contig based on sequence alignment, if the BAC is sequenced, or via the alignment of its BAC fingerprint to the fingerprints of other BACs. The assemblies can be found using the Maize Genome Browser, which is publicly available on the internet.

An allele is "associated with" a trait when it is linked to it and when the presence of the allele is an indicator that the desired trait or trait form will occur in a plant comprising the allele.

The "B73 reference genome, version 2" is the physical and genetic framework of the maize B73 genome. It is the result of a sequencing effort utilizing a minimal tiling path of approximately 19,000 mapped BAC clones, and focusing on producing high-quality sequence coverage of all identifiable gene-containing regions of the maize genome. These regions were ordered, oriented, and along with all of the intergenic sequences, anchored to the extant physical and genetic maps of the maize genome. It can be accessed using a genome browser, the Maize Genome Browser, which is publicly available on the internet that facilitates user interaction with sequence and map data.

A "BAC," or bacterial artificial chromosome, is a cloning vector derived from the naturally occurring F factor of *Escherichia coli*. BACs can accept large inserts of DNA sequence. In maize, a number of BACs, or bacterial artificial chromosomes, each containing a large insert of maize genomic DNA, have been assembled into contigs (overlapping contiguous genetic fragments, or "contiguous DNA").

"Backcrossing" refers to the process whereby hybrid progeny are repeatedly crossed back to one of the parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. (1995) Marker-assisted backcrossing: a practical example, in Techniques et Utilisations des Marqueurs Moleculaires Les Colloques, Vol. 72, pp. 45-56, and Openshaw et al., (1994) Marker-assisted Selection in Backcross Breeding, Analysis of Molecular Marker Data, pp. 41-43. The initial cross gives rise to the F1 generation: the term "BC1" then refers to the second use of the recurrent parent, "BC2" refers to the third use of the recurrent parent, and so on.

A centimorgan ("cM") is a unit of measure of recombination frequency. One cM is equal to a 1% chance that a marker at one genetic locus will be separated from a marker at a second locus due to crossing over in a single generation.

"Chromosomal interval" designates a contiguous linear span of genomic DNA that resides in plants on a single chromosome. The genetic elements or genes located on a single chromosomal interval are physically linked. The size of a chromosomal interval is not particularly limited. In some aspects, the genetic elements located within a single chromosomal interval are genetically linked, typically with a genetic recombination distance of, for example, less than or equal to 20 cM, or alternatively, less than or equal to 10 cM. That is, two genetic elements within a single chromosomal interval undergo recombination at a frequency of less than or equal to 20% or 10% respectively.

The term "chromosomal interval" designates any and all intervals defined by any of the markers set forth in this invention. A chromosomal interval that correlates with decreased MRCV is provided. One such interval, located on chromosome 4, comprises and is flanked by PZD00030.2 and DAS-PZ-7622. A subinterval of chromosomal interval PZD00030.2 and DAS-PZ-7622 is DAS-PZ-4588 and MAGI_75461.

The term "complement" refers to a nucleotide sequence that is complementary to a given nucleotide sequence, i.e., the sequences are related by the base-pairing rules.

The term "contiguous DNA" refers to overlapping contiguous genetic fragments.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

The term "elite line" refers to any line that has resulted from breeding and selection for superior agronomic performance. An elite plant is any plant from an elite line.

A "favorable allele" is the allele at a particular locus that confers, or contributes to, a desirable phenotype, e.g., decreased MRCV, or alternatively, is an allele that allows the identification of plants with increased MRCV that can be removed from a breeding program or planting ("counter-selection"). A favorable allele of a marker is a marker allele that segregates with the favorable phenotype, or alternatively, segregates with the unfavorable plant phenotype, therefore providing the benefit of identifying plants.

"Fragment" is intended to mean a portion of a nucleotide sequence. Fragments can be used as hybridization probes or PCR primers using methods disclosed herein.

A "genetic map" is a description of genetic linkage relationships among loci on one or more chromosomes (or chromosomes) within a given species, generally depicted in a diagrammatic or tabular form. For each genetic map, distances between loci are measured by the recombination frequencies between them, and recombinations between loci can be detected using a variety of molecular genetic markers (also called molecular markers). A genetic map is a product of the mapping population, types of markers used, and the polymorphic potential of each marker between different populations. The order and genetic distances between loci can differ from one genetic map to another. However, information such as marker position and order can be correlated between maps by determining the physical location of the markers on the chromosome of interest, using the B73 reference genome, version 2, which is publicly available on the internet. One of ordinary skill in the art can use the publicly available genome browser to determine the physical location of markers on a chromosome.

The term "Genetic Marker" shall refer to any type of nucleic acid based marker, including but not limited to, Restriction Fragment Length Polymorphism (RFLP), Simple Sequence Repeat (SSR), Random Amplified Polymorphic DNA (RAPD), Cleaved Amplified Polymorphic Sequences (CAPS) (Rafalski and Tingey, 1993, Trends in Genetics 9:275-280), Amplified Fragment Length Polymorphism (AFLP) (Vos et al, 1995, Nucleic Acids Res. 23:4407-4414), Single Nucleotide Polymorphism (SNP) (Brookes, 1999, Gene 234:177-186), Sequence Characterized Amplified Region (SCAR) (Pecan and Michelmore, 1993, Theor. Appl. Genet, 85:985-993), Sequence Tagged Site (STS) (Onozaki et al. 2004, Euphytica 138:255-262), Single Stranded Conformation Polymorphism (SSCP) (Orita et al., 1989, Proc Natl Aced Sci USA 86:2766-2770). Inter-Simple Sequence Repeat (ISR) (Blair et al. 1999, Theor. Appl. Genet. 98:780-792), Inter-Retrotransposon Amplified Polymorphism (IRAP), Retrotransposon-Microsatellite Amplified Polymorphism (REMAP) (Kalendar et al., 1999, Theor. Appl. Genet 98:704-711), an RNA cleavage product (such as a Lynx tag), and the like.

"Genetic recombination frequency" is the frequency of a crossing over event (recombination) between two genetic loci. Recombination frequency can be observed by following the segregation of markers and/or traits following meiosis.

"Genome" refers to the total DNA, or the entire set of genes, carried by a chromosome or chromosome set.

The term "genotype" is the genetic constitution of an individual (or group of individuals) at one or more genetic loci, as contrasted with the observable trait (the phenotype). Genotype is defined by the allele(s) of one or more known loci that the individual has inherited from its parents. The term genotype can be used to refer to an individual's genetic constitution at a single locus, at multiple led, or, more generally, the term genotype can be used to refer to an individual's genetic make-up for all the genes in its genome.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells that can be cultured into a whole plant.

A "haplotype" is the genotype of an individual at a plurality of genetic loci, i.e. a combination of alleles. Typically, the genetic loci described by a haplotype are physically and genetically linked, i.e., on the same chromosome segment. The term "haplotype" can refer to sequence, polymorphisms at a particular locus, such as a single marker locus, or sequence polymorphisms at multiple loci along a chromosomal segment in a given genome. The former can also be referred to as "marker haplotypes" or "marker alleles," while the latter can be referred to as "long-range haplotypes."

The "heritability ($h^2$)" of a trait within a population is the proportion of observable differences in a trait between individuals within a population that is due to genetic differences. The $h^2$ value of the QTL is a percentage of variation that is explained by genetics, instead of environment.

A "heterotic group" comprises a set of genotypes that perform well when crossed with genotypes from a different heterotic group (Hallauer at al. (1998) Corn breeding, p. 463-564. In G. F. Sprague and J. W. Dudley (ed) Corn and corn improvement). Inbred lines are classified into heterotic groups, and are further subdivided into families within a heterotic group, based on several criteria such as pedigree, molecular marker-based associations, and performance in hybrid combinations (Smith at al. (1990) Theor. Appl. Gen. 80:833-840). The two most widely used heterotic groups in the United States are referred to as "Iowa Stiff Stalk Synthetic" (BSSS) and "Lancaster" or "Lancaster Sure Crop" (sometimes referred to as NSS, or Iron-Stiff Stalk).

The term "heterozygous" means a genetic condition wherein different alleles reside at corresponding loci on homologous chromosomes.

The term "homozygous" means a genetic condition wherein identical alleles reside at corresponding loci on homologous chromosomes.

"Hybridization" or "nucleic acid hybridization" refers to the pairing of complementary RNA and DNA strands as well as the pairing of complementary DNA single strands.

The term "hybridize" means the formation of base pairs between complementary regions of nucleic acid strands.

The term "indel" refers to an insertion or deletion, wherein one line may be referred to as having an insertion relative to a second line, or the second line may be referred to as having a deletion relative to the first line.

The term "introgression" or "introgressing" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background. For example, the chromosome 4 locus described herein may be introgressed into a recurrent parent that has problematic MRCV. The recurrent parent line with the introgressed gene or locus then has decreased MRCV.

As used herein, the term "linkage" is used to describe the degree with which one marker locus is associated with another marker locus or some other locus (for example, a MRCV locus). The linkage relationship between a molecular marker and a phenotype is given as a "probability" or "adjusted probability." Linkage can be expressed as a desired limit or range. For example, in some embodiments, any marker is linked (genetically and physically) to any other marker when the markers are separated by less than 50, 40, 30, 25, 20, or 15 map units for cM). In some aspects, it is advantageous to define a bracketed range of linkage, for example, between 10 and 20 cM, between 10 and 30 cM, or between 10 and 40 cM. The more closely a marker is linked to a second locus, the better an indicator for the second locus that marker becomes. Thus, "closely linked loci" such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10 (e.g., about 9%, 8%, 7%, 6%, 5%, 4%, 3%, 2%, 1%, 0.75%, 0.5%, 0.25%, or less) are also said to be "proximal to" each other. Since one cM is the distance between two markers that show a 1% recombination frequency, any marker is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

The term "linkage disequilibrium" refers to a non-random segregation of genetic loci, traits, or both. In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and by definition, are separated by less than 50 cM on the same chromosome.) As used herein, linkage can be between two markers, or alternatively between a marker and a phenotype. A marker locus can be "associated with" (linked to) a trait, e.g., decreased MRCV. The degree of linkage of a molecular marker to a phenotypic trait is measured, e.g. as a statistical probability of co-segregation of that molecular marker with the phenotype.

Linkage disequilibrium is most commonly assessed using the measure $r^2$, which is calculated using the formula described by Hill, W. G. and Robertson, A, Theor Appl. Genet 38:226-231 (1988). When $r^2=1$, complete LD exists between the two marker loci, meaning that the markers have not been separated by recombination and have the same allele frequency. Values for $r^2$ above 0.33 indicate sufficiently strong LD to be useful for mapping (Ardlie at al., Nature Reviews Genetics 3:299-309 (2002)). Hence, alleles are in linkage disequilibrium when $r^2$ values between pair-wise marker loci are greater than or equal to 0.33, 0.4, 0.5, 0.6, 0.7, 0.8, 0.9, or 1.0.

As used herein, "linkage equilibrium" describes a situation where two markers independently segregate, i.e., sort among progeny randomly. Markers that show linkage equilibrium are considered unlinked (whether or not they lie on the same chromosome).

The term "lodge" is synonymous with break. Hence, stalks that lodge are those that break at a position along the stalk.

The "logarithm of odds (LOD) value" or "LOD score" (Risch, Science 255:803-804 (1992)) is used in interval mapping to describe the degree of linkage between two marker loci. A LOD score of three between two markers indicates that linkage is 1000 times more likely than no linkage, while a LOD score of two indicates that linkage is 100 times more likely than no linkage. LOD scores greater than or equal to two may be used to detect linkage.

A "locus" is a position on a chromosome where a gene or marker is located.

"Maize" refers to a plant of the *Zea mays* L. ssp. *mays* and is also known as "corn."

The term "maize plant" includes: whole maize plants, maize plant cells, maize plant protoplast, maize plant cell or maize tissue cultures from which maize plants can be regenerated, maize plant calli, and maize plant cells that are intact in maize plants or parts of maize plants, such as maize seeds, maize cobs, maize flowers, maize cotyledons, maize leaves, maize stems, maize buds, maize roots, maize root tips, and the like.

"Mal de Rio Cuarto Virus (MRCV)" is a species of virus in the Reoviridae family, genus *Fijivirus*, which causes devastating crop losses for producers in Argentina.

A "marker" is a nucleotide sequence or encoded product thereof (e.g., a protein) used as a point of reference. For markers to be useful at detecting recombinations, they need to detect differences, or polymorphisms, within the population being monitored. For molecular markers, this means differences at the DNA level due to polynucleotide sequence differences (e.g. SSRs, RFLPs, FLPs, SNPs). The genomic variability can be of any origin, for example, insertions, deletions, duplications, repetitive elements, point mutations, recombination events, or the presence and sequence of transposable elements. Molecular markers can be derived from genomic or expressed nucleic acids (e.g., ESTs) and can also refer to nucleic acids used as probes or primer pairs capable of amplifying sequence fragments via the use of PCR-based methods. A large number of maize molecular markers are known in the art, and are published or available from various sources, such as the Maize GDB Internet resource and the Arizona Genomics Institute Internet resource run by the University of Arizona.

Markers corresponding to genetic polymorphisms between members of a population can be detected by methods well-established in the art. These include, e.g., DNA sequencing, PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also known for the detection of expressed sequence tags (ESTs) and SSR markers derived from EST sequences and randomly amplified polymorphic DNA (RAPD).

A "marker allele," alternatively an "allele of a marker locus," can refer to one of a plurality of polymorphic nucleotide sequences found at a marker locus in a population that is polymorphic for the marker locus.

"Marker assisted selection" (or MAS) is a process by which phenotypes are selected based on marker genotypes.

"Marker assisted counter-selection" is a process by which marker genotypes are used to identify plants that will not be selected, allowing them to be removed from a breeding program or planting.

A "marker locus" is a specific chromosome location in the genome of a species when a specific marker can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

A "marker probe" is a nucleic add sequence or molecule that can be used to identify the presence of a marker locus, e.g., a nucleic acid probe that is complementary to a marker locus sequence, through nucleic add hybridization. Marker probes comprising 30 or more contiguous nucleotides of the marker locus ("all or a portion" of the marker locus sequence) may be used for nucleic acid hybridization. Alternatively, in some aspects, a marker probe refers to a probe of any type that is able to distinguish (i.e. genotype) the particular allele that is present at a marker locus.

The term "molecular marker" may be used to refer to a genetic marker, as defined above, or an encoded product thereof (e.g., a protein) used as a point of reference when identifying a linked locus. A marker can be derived from genomic nucleotide sequences or from expressed nucleotide sequences (e.g., from a spliced RNA, a cDNA, etc.), or from an encoded polypeptide. The term also refers to nucleic acid sequences complementary to or flanking the marker sequences, such as nucleic acids used as probes or primer pairs capable of amplifying the marker sequence. A "molecular marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. Nucleic acids are "complementary" when they specifically hybridize in solution, e.g., according to Watson-Crick base pairing rules. Some of the markers described herein are also referred to as hybridization markers when located on an indel region, such as the non-collinear region described herein. This is because the insertion region is, by definition, a polymorphism vis a via a plant without the insertion. Thus, the marker need only indicate whether the indel region is present or absent. Any suitable marker detection technology may be used to identify such a hybridization marker, e.g., SNP technology is used in the examples provided herein.

"Nucleotide sequence," "polynucleotide," "nucleic acid sequence," and "nucleic acid fragment" are used interchangeably and refer to a polymer of RNA or DNA that is single- or double-stranded, optionally containing synthetic, non-natural or altered nucleotide bases. A "nucleotide" is a monomeric unit from which DNA or RNA polymers are constructed, and consists of a purine or pyrimidine base, a pentose, and a phosphoric acid group. Nucleotides (usually found in their 5'-monophosphate form) are referred to by their single letter designation as follows: "A" for adenylate or deoxyadenylate (for RNA or DNA, respectively), "C" for cytidylate or deoxycytidylate. "G" for guanylate or deoxyguanylate. "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "phenotype," or "phenotypic trait" or "trait" refers to one or more traits of an organism. The phenotype can be observable to the naked eye, or by any other means of evaluation known in the art, e.g., microscopy, biochemical analysis, or an electromechanical assay. In some cases, a phenotype is directly controlled by a single gene or genetic locus, i.e., a "single gene trait." In other cases, a phenotype is the result of several genes.

A "physical map" of the genome is a map showing the linear order of identifiable landmarks (including genes, markers, etc.) on chromosome DNA. However, in contrast to genetic maps, the distances between landmarks are absolute (for example, measured in base pairs or isolated and overlapping contiguous genetic fragments) and not based on genetic recombination.

A "plant" can be a whole plant, any part thereof, or a cell or tissue culture derived from a plant. Thus, the term "plant" can refer to any of: whole plants, plant components or organs (e.g., leaves, stems, roots, etc.), plant tissues, seeds, plant cells, and/or progeny of the same. A plant cell is a cell of a plant, taken from a plant, or derived through culture from a cell taken from a plant.

A "polymorphism" is a variation in the DNA that is too common to be due merely to new mutation. A polymorphism must have a frequency of at least 1% in a population. A polymorphism can be a single nucleotide polymorphism, or SNP, or an insertion/deletion polymorphism, also referred to herein as an "indel."

The "probability value" or "p-value" is the statistical likelihood that the particular combination of a phenotype and the presence or absence of a particular marker allele is random. Thus, the lower the probability score, the greater the likelihood that a phenotype and a particular marker will co-segregate. In some aspects, the probability score is considered "significant" or "non-significant." In some embodiments, a probability score of 0.05 (p=0.05, or a 5% probability) of random assortment is considered a significant indication of co-segregation. However, an acceptable probability can be any probability of less than 50% (p=0.5). For example, a significant probability can be less than 0.25, less than 0.20, less than 0.15, less than 0.1, less than 0.05, less than 0.01, or less than 0.001.

The term "progeny" refers to the offspring generated from a cross.

A "progeny plant" is generated from a cross between two plants.

A "reference sequence" is a defined sequence used as a basis for sequence comparison. The reference sequence is obtained by genotyping a number of lines at the locus, aligning the nucleotide sequences in a sequence alignment program (e.g. Sequencher), and then obtaining the consensus sequence of the alignment.

A "single nucleotide polymorphism (SNP)" is a DNA sequence variation occurring when a single nucleotide—A, T, C or G—in the genome (or other shared sequence) differs between members of a biological species or paired chromosomes in an individual. For example, two sequenced DNA fragments from different individuals, AAGCCTA to AAGCTTA, contain a difference in a single nucleotide.

The "Non-Stiff Stalk" heterotic group represents a major temperate heterotic group. It can also be referred to as the non-Iowa Stiff Stalk Synthetic for BSSS (non-BSSS) heterotic group.

The phrase "under stringent conditions" refers to conditions under which a probe or polynucleotide will hybridize to a specific nucleic acid sequence, typically in a complex mixture of nucleic acids, but to essentially no other sequences. Stringent conditions are sequence-dependent and will be different in different circumstances.

Sequence alignments and percent identity calculations may be determined using a variety of comparison methods designed to detect homologous sequences including, but not limited to, the MEGALIGN® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp, CABIOS. 5:151-153 (1989)) with the default parameters (GAP PENALTY=10, GAP LENGTH PENALTY=10), Default parameters for pairwise alignments and calculation of percent identity of protein sequences using the Clustal V method are KTUPLE=1, GAP PENALTY=3, WINDOW=5 and DIAGONALS SAVED=5. For nucleic adds these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Before describing the present invention in detail, it should be understood that this invention is not limited to particular embodiments. It also should be understood that the terminology used herein is for the purpose of describing particular embodiments, and is not intended to be limiting. As used herein and in the appended claims, terms in the singular and the singular forms "a," "an," and "the," for example, include plural referents unless the content clearly dictates otherwise. Thus, for example, reference to "plant," "the plant," or "a plant" also includes a plurality of plants. Depending on the context, use of the term "plant" can also include genetically similar or identical progeny of that plant. The use of the term "a nucleic acid" optionally includes many copies of that nucleic acid molecule.

Genetic Mapping

It has been recognized for quite some time that specific genetic loci correlating with particular phenotypes, such as reduced MRCV, can be mapped in an organism's genome. The plant breeder can advantageously use molecular markers to identify desired individuals by detecting marker alleles that show a statistically significant probability of co-segregation with a desired phenotype, manifested as linkage disequilibrium. By identifying a molecular marker or clusters of molecular markers that co-segregate with a trait of interest, the breeder is able to rapidly select a desired phenotype by selecting for the proper molecular marker allele (a process called marker-assisted selection, or MAS).

A variety of methods well known in the art are available for detecting molecular markers or clusters of molecular markers that co-segregate with a trait of interest, such as reduced MRCV. The basic idea underlying these methods is the detection of markers, for which alternative genotypes (or alleles) have significantly different average phenotypes. Thus, one makes a comparison among marker loci of the magnitude of difference among alternative genotypes (or alleles) or the level of significance of that difference. Trait genes are inferred to be located nearest the marker(s) that have the greatest associated genotypic difference.

Two such methods used to detect trait loci of interest are: 1) Population-based association analysis and 2) Traditional linkage analysis. In a population-based association analysis, lines are obtained from pre-existing populations with multiple founders, e.g. elite breeding lines. Population-based association analyses rely on the decay of linkage disequilibrium (LD) and the idea that in an unstructured population, only correlations between genes controlling a trait of interest and markers closely linked to those genes will remain after so many generations of random mating. In reality, most pre-existing populations have population substructure. Thus, the use of a structured association approach helps to control population structure by allocating individuals to populations using data obtained from markers randomly distributed across the genome, thereby minimizing disequilibrium due to population structure within the individual populations (also called subpopulations). The phenotypic values are compared to the genotypes (alleles) at each, marker locus for each line in the subpopulation. A significant marker-trait association indicates the dose proximity between the marker locus and one or more genetic loci that are involved in the expression of that trait.

The same principles underlie traditional linkage analysis; however, LD is generated by creating a population from a small number of founders. The founders are selected to maximize the level of polymorphism within the constructed population, and polymorphic sites are assessed for their level of co-segregation with a given phenotype. A number of statistical methods have been used to identify significant marker-trait associations. One such method is an interval mapping approach (Lander and Botstein, Genetics 121:185-199 (1989), in which each of many positions along a genetic map (say at 1 cM intervals) is tested for the likelihood that a gene controlling a trait of interest is located at that position. The genotype/phenotype data are used to calculate for each test position a LOD score (log of likelihood ratio). When the LOD score exceeds a threshold value, there is significant evidence for the location of a gene controlling the trait of interest at that position on the genetic map (which will fall between two particular marker loci).

Markers Associated with MRCV Resistance

Markers associated with MRCV resistance are identified herein. The methods involve detecting the presence of at least one marker allele associated with the enhanced resistance in the germplasm of a maize plant. The marker locus can be selected from any of the marker loci on chromosome 4 provided in Table 3, including DAS-PZ-4588, MAGI_38007, DAS-PZ-12232, and MAGI_75461, and any other marker linked to these markers (linked markers can be determined from the Maize GDB resource). The marker locus can be selected from any of the marker loci on chromosome 4 provided in Table 3, including PZD00030.2, PZA02194-1, PZE-104104856, Mo17-14216, DAS-PZ-19059, PZE-104109680, PZE-104110452, PZB01461.2, PZA02614.2, chr4_206864219, KG-2634304, DAS-PZ-9024, DAS-PZ-11829, PZE-104135467, PZE-104136149, MAGI_73697, PZE-104137851, DAS-PZ-236, DAS-PZ-7082, MAGI_35446, DAS-PZ-12609, and DAS-PZ-7622 and any other marker linked to this marker (linked markers can be determined from the MaizeGDB resource).

Additionally, the marker locus can be selected from any of the marker loci on chromosome 5 provided in Table 3, including PZB02059.2, PZE-105084059, DAS-PZ-20613, and PZA01608-1, and any other marker linked to these markers (linked markers can be determined from the Maize GDB resource). The marker locus can be selected from any of the marker loci on chromosome 5 provided in Table 3, including DAS-PZ-8199, Mo17-11151, DAS-PZ-10982, PZE-105106594, DAS-PZ-15377, and MAGI_105022-2 and any other marker linked to this marker (linked markers can be determined from the Maize GDB resource).

Additionally, the marker locus can be selected from any of the marker loci on chromosome 5 provided in Table 3, including PZA02015-11, PZA03167.5, and PZE-105166278, and any other marker linked to these markers (linked markers can be determined from the Maize GDB resource). The marker locus can be selected from any of the marker loci on chromosome 5 provided in Table 3, including PZE-105159825, PZE-105160788, PZA00545.26, and PZE-105169090, and any other marker linked to this marker (linked markers can be determined from the Maize GDB resource).

The genetic elements or genes located on a contiguous linear span of genomic DNA on a single chromosome are physically linked. PZD00030.2 and DAS-PZ-7622, both highly associated with MRCV resistance, delineate a MRCV resistance QTL. Any polynucleotide that assembles to the contiguous DNA between and including SEQ ID NO:1 (the reference sequence for PZD00030.2), or a nucleotide sequence that is 95% identical to SEQ ID NO:1 based on the Clustal V method of alignment, and SEQ ID NO:26 (the reference sequence for DAS-PZ-7622), or a nucleotide sequence that is 95% identical to SEQ ID NO:26 based on the Clustal V method of alignment, can house marker loci that are associated with MRCV resistance.

The genetic elements or genes located on a contiguous linear span of genomic DNA on a single chromosome are physically linked for the subinterval of DAS-PZ-4588 and MAGI_75461. DAS-PZ-4588 and MAGI_75461, both highly associated with MRCV resistance, delineate a MRCV resistance QTL. Any polynucleotide that assembles to the contiguous DNA between and including SEQ ID NO:9 (the reference sequence for DAS-PZ-4588), or a nucleotide sequence that is 95% identical to SEQ ID NO:9 based on the Clustal V method of alignment, and SEQ ID NO:12 (the reference sequence for MAGI_75461), or a nucleotide sequence that 95% identical to SEQ ID NO:12 based on the Clustal V method of alignment, can house marker loci that are associated with MRCV resistance.

The genetic elements or genes located on a contiguous linear span of genomic DNA on a single chromosome are physically linked. DAS-PZ-8199 and MAGI_105022-2, both highly associated with MRCV resistance, delineate a MRCV resistance QTL. Any polynucleotide that assembles to the contiguous DNA between and including SEQ ID NO:34 (the reference sequence for DAS-PZ-8199), or a nucleotide sequence that is 95% identical to SEQ ID NO:34 based on the Clustal V method of alignment, and SEQ ID NO:43 (the reference sequence for MAGI_105022-2), or a nucleotide sequence that is 95% identical to SEQ ID NO:43 based on the Clustal V method of alignment, can house marker loci that are associated with MRCV resistance.

The genetic elements or genes located on a contiguous linear span of genomic DNA on a single chromosome are physically linked for the subinterval of PZB02059.2 and PZA01608-1. PZB02059.2 and PZA01608-1, both highly associated with MRCV resistance, delineate a MRCV resistance QTL. Any polynucleotide that assembles to the contiguous DNA between and including SEQ ID NO:36 (the reference sequence for PZB02059.2), or a nucleotide sequence that is 95% identical to SEQ ID NO:36 based on the Clustal V method of alignment, and SEQ ID NO:39 (the reference sequence for PZA01608-1), or a nucleotide sequence that 95% identical to SEQ ID NO:39 based on the Clustal V method of alignment, can house marker loci that are associated with MRCV resistance.

The genetic elements or genes located on a contiguous linear span of genomic DNA on a single chromosome are physically linked. PZE-105159825 and PZE-105169090, both highly associated with MRCV resistance, delineate a MRCV resistance QTL. Any polynucleotide that assembles to the contiguous DNA between and including SEQ ID NO:27 (the reference sequence for PZE-105159825), or a nucleotide sequence that is 95% identical to SEQ ID NO:27 based on the Clustal V method of alignment, and SEQ ID NO:33 (the reference sequence for PZE-105169090), or a nucleotide sequence that is 95% identical to SEQ ID NO:33 based on the Clustal V method of alignment, can house marker loci that are associated with MRCV resistance.

The genetic elements or genes located on a contiguous linear span of genomic DNA on a single chromosome are physically linked for the subinterval of PZA02015-11 and PZE-105166278. PZA02015-11 and PZE-105166278, both highly associated with MRCV resistance, delineate a MRCV resistance QTL. Any polynucleotide that assembles to the contiguous DNA between and including SEQ ID NO:30 (the reference sequence for PZA02015-11), or a nucleotide sequence that is 95% identical to SEQ ID NO:30 based on the Clustal V method of alignment, and SEQ ID NO:32 (the reference sequence for PZE-105166278), or a nucleotide sequence that 95% identical to SEQ ID NO:32 based on the Clustal V method of alignment, can house marker loci that are associated with MRCV resistance.

A common measure of linkage is the frequency with which traits co-segregate. This can be expressed as a percentage of co-segregation (recombination frequency) or in centiMorgans (cM). The cM is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency.

Marker loci are themselves traits and can be assessed according to standard linkage analysis by tracking the marker loci during segregation. Thus, one cM is equal to a 1% chance that a marker locus will be separated from another locus, due to crossing over in a single generation.

Other markers linked to the markers listed in Table 3 can be used to predict MRCV resistance in a maize plant. This includes any marker within 50 cM of PZD00030.2, PZA02194-1, PZE-104104856, Mo17-14216, DAS-PZ-19059, PZE-104109680, PZE-104110452, PZB01461.2, DAS-PZ-4588, MAGI_38007, DAS-PZ-12232, MAGI_75461, PZA02614.2, chr4_206864219, KG-2634304, DAS-PZ-9024, DAS-PZ-11829, PZE-104135467, PZE-104136149, MAGI_73697, PZE-104137851, DAS-PZ-236, DAS-PZ-7082, MAGI_35446, DAS-PZ-12609, and DAS-PZ-7622, the markers associated with the MRCV resistance. This also includes any marker within 50 cM of DAS-PZ-8199, Mo17-11151, PZB02059.2, PZE-105084059, DAS-PZ-20613, PZA01608-1, DAS-PZ-10982, PZE-105106594, DAS-PZ-15377, and MAGI_105022-2, the markers associated with the MRCV resistance. Any marker that is within 50 cM of PZE-105159825, PZE-105160788, PZA00545.26, PZA02015-11, PZA03167.5, PZE-105166278, and PZE-105169090, the markers associated with the MRCV resistance, is also included. The closer a marker is to a gene controlling a trait of interest, the more effective and advantageous that marker is as an indicator for the desired trait. Closely linked loci display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus) display a recombination frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of less than 10% (e.g., about 9%, 8% 7%, 6%, 5%, 4%, 3%, 2% 1%, 0.75%, 0.5%, 0.25 degree, or less) are said to be "proximal to" each other.

Although particular marker alleles can show co-segregation with increased MRCV resistance, it is important to note that the marker locus is not necessarily responsible for the expression of the MRCV resistance phenotype. For example, it is not a requirement that the marker polynucleotide sequence be part of a gene that imparts increased MRCV resistance (for example, be part of the gene open reading frame). The association between a specific marker allele and the increased MRCV resistance phenotype is due to the original "coupling" linkage phase between the marker allele and the allele in the ancestral maize line from which the allele originated. Eventually, with repeated recombination, crossing over events between the marker and genetic locus can change this orientation. For this reason, the favorable marker allele may change depending on the linkage phase that exists within the resistant parent used to create segregating populations. This does not change the fact that the marker can be used to monitor segregation of the phenotype. It only changes which marker allele is considered favorable in a given segregating population.

The term "chromosomal interval" designates any and all intervals defined by any of the markers set forth in this invention. Three chromosomal intervals that correlate with MRCV resistance are provided. One interval, located on chromosome 4, comprises and is flanked by PZD00030.2 and DAS-PZ-7622. A subinterval of chromosomal interval by PZD00030.2 and DAS-PZ-7622 is DAS-PZ-4588 and MAGI_75461. Another interval, located on chromosome 5, comprises and is flanked by DAS-PZ-8199 and MAGI_105022-2. A subinterval of chromosomal interval by DAS-PZ-8199 and MAGI_105022-2 is PZB02059.2 and PZA01608-1. A third interval, located on chromosome 5, comprises and is flanked by PZE-105159825 and PZE-105169090. A subinterval of chromosomal interval by PZE-105159825 and PZE-105169090 is PZA02015-11 and PZE-105166278.

A variety of methods well known in the art are available for identifying chromosomal intervals. The boundaries of such chromosomal intervals are drawn to encompass markers that will be linked to the gene controlling the trait of interest. In other words, the chromosomal interval is drawn such that any marker that lies within that interval (including the terminal markers that define the boundaries of the interval) can be used as a marker for MRCV resistance. The interval described above encompasses a cluster of markers that co-segregate with MRCV resistance. The clustering of markers occurs in relatively small domains on the chromosomes, indicating the presence of a gene controlling the trait of interest in those chromosome regions. The interval was drawn to encompass the markers that co-segregate with MRCV resistance. The interval encompasses markers that map within the interval as well as the markers that define the termini. For example, PZD00030.2 and DAS-PZ-7622, separated by 56027420 bp based on the B73 reference genome, version 2, define a chromosomal interval encompassing a cluster of markers that co-segregate with MRCV resistance. A second example includes the subinterval, DAS-PZ-4588 and MAGI_75461, separated by 9270051 bp based on the B73 reference genome, version 2, that defines a chromosomal interval encompassing a cluster of markers that co-segregate with MRCV resistance. An interval described by the terminal markers that define the endpoints of the interval will include the terminal markers and any marker localizing within that chromosomal domain, whether those markers are currently known or unknown.

Chromosomal intervals can also be defined by markers that are linked to (show linkage disequilibrium with) a marker of interest, and is a common measure of linkage disequilibrium (LD) in the context of association studies. If the $r^2$ value of LD between any chromosome 4 marker locus lying within the interval of PZD00030.2 and DAS-PZ-7622, the subinterval of DAS-PZ-4588 and MAGI_75461, or any other subinterval of PZD00030.2 and DAS-PZ-7622, and an identified marker within that interval that has an allele associated with increased MRCV resistance is greater than ⅓ (Ardlie et al. Nature Reviews Genetics 3:299-309 (2002)), the loci are linked. If the $r^2$ value of LD between any chromosome 5 marker locus lying within the interval of DAS-PZ-8199 and MAGI_105022-2, the subinterval of PZB02059.2 and PZA01608-1, or any other subinterval of DAS-PZ-8199 and MAGI_105022-2, and an identified marker within that interval that has an allele associated with increased MRCV resistance is greater than ⅓, the loci are linked. If the $r^2$ value of LD between any chromosome 5 marker locus lying within the interval of PZE-105159825 and PZE-105169090, the subinterval of PZA02015-11 and PZE-105166278, or any other subinterval of PZE-105159825 and PZE-105169090, and an identified marker within that interval that has an allele associated with increased MRCV resistance is greater than ⅓, the loci are linked.

A marker of the invention can also be a combination of alleles at marker loci, otherwise known as a haplotype. The skilled artisan would expect that there might be additional polymorphic sites at marker loci in and around the chromosome 4 and 5 markers identified herein, wherein one, or more polymorphic sites is in linkage disequilibrium (LD) with an allele associated with increased MRCV resistance. Two particular alleles at different polymorphic sites are said to be in LD if the presence of the allele at one of the sites tends to predict the presence of the allele at the other site on the same chromosome (Stevens, Mol. Diag. 4:309-17 (1999)).

Marker Assisted Selection

Molecular markers can be used in a variety of, plant breeding applications (e.g. see Staub et al. (1996) Hortscience 729-741; Tanksley (1983) Plant Molecular Biology Reporter 1: 3-8). One of the main areas of interest is to increase the efficiency of backcrossing and introgressing genes using marker-assisted selection (MAS). A molecular marker that demonstrates linkage with a locus affecting a desired phenotypic trait provides a useful tool for the selection of the trait in a plant population. This is particularly true where the phenotype is hard to assay, e.g. many disease resistance traits, or, occurs at a late stage in plant development, e.g. kernel characteristics. Since DNA marker assays are less laborious and take up less physical space than field phenotyping, much larger populations can be assayed, increasing the chances of finding a recombinant with the target segment from the donor line moved to the recipient line. The closer the linkage, the more useful the marker, as recombination is less likely to occur between the marker and the gene causing the trait, which can result in false positives. Having flanking markers decreases the chances that false positive selection will occur as a double recombination event would be needed. The ideal situation is to have a marker in the gene itself, so that recombination cannot occur between the marker and the gene. Such a marker is called a "perfect marker."

When a gene is introgressed by MAS, it is not only the gene that is introduced but also the flanking regions (Gepts. (2002). Crop Sci; 42: 1780-1790). This is referred to as "linkage drag." In the case where the donor plant is highly unrelated to the recipient plant, these flanking regions carry additional genes that may code for agronomically undesirable traits. This "linkage drag" may also result in reduced yield or other negative agronomic characteristics even after multiple cycles of backcrossing into the elite maize line. This is also sometimes referred to as "yield drag." The size of the flanking region can be decreased by additional backcrossing, although this is not always successful, as breeders do not have control over the size of the region or the recombination breakpoints (Young et al, (1998) Genetics 120:579-585). In classical breeding it is usually only by chance that recombinations are selected that contribute to a reduction in the size of the donor segment (Tanksley et al. (1989). Biotechnology 7: 257-264). Even after 20 backcrosses in backcrosses of this type, one may expect to find a sizeable piece of the donor chromosome still linked to the gene being selected. With markers however, it is possible to select those rare individuals that have experienced recombination near the gene of interest. In 150 backcross plants, there is a 95% chance that at least one plant will have experienced a crossover within 1 cM of the gene, based on a single meiosis map distance. Markers will avow unequivocal identification of those individuals. With one additional backcross of 300 plants, there would be a 95% chance of a crossover within 1 cM single meiosis map distance of the other side of the gene, generating a segment around the target gene of less than 2 cM based on a single meiosis map distance. This can be accomplished in two generations with markers, while it would have required on average 100 generations without markers (See Tanksley et al., supra). When the exact location of a gene is known, flanking markers surrounding the gene can be utilized to select for recombinations in different population sizes. For example, in smaller population sizes, recombinations may be expected further away from the gene, so more distal flanking markers would be required to detect the recombination.

The availability of the B73 reference genome, version 2 and the integrated linkage maps of the maize genome containing increasing densities of public maize markers, has facilitated maize genetic mapping and MAS. See, e.g. the IBM2 Neighbors maps, which are available online on the Maize GDB website.

The key components to the implementation of MAS are (i) Defining the population within which the marker-trait association will be determined, which can be a segregating population, or a random or structured population; (ii) monitoring the segregation or association of polymorphic markers relative to the trait, and determining linkage or association using statistical methods; (iii) defining a set of desirable markers based on the results of the statistical analysis, and (iv) the use and/or extrapolation of this information to the current set of breeding germplasm to enable marker-based selection decisions to be made. The markers described in this disclosure, as well as other marker types such as SSRs and FLPs, can be used in marker assisted selection protocols.

SSRs can be defined as relatively short runs of tandemly repeated DNA with lengths of 6 bp or less (Tautz (1989) Nucleic Acid Research 17: 6463-6471; Wang et al. (1994) Theoretical and Applied Genetics, 88:1-6) Polymorphisms arise due to variation in the number of repeat units, probably caused by slippage during DNA replication (Levinson and Gutman (1987) Mol Biol Evol 4: 203-221). The variation in repeat length may be detected by designing PCR primers to the conserved non-repetitive flanking regions (Weber and May (1989) Am J Hum Genet. 44:388-396). SSRs are highly suited to mapping and MAS as they are multi-allelic, codominant, reproducible and amenable to high throughput automation (Rafalski et al. (1996) Generating and using DNA markers in plants. In Non-mammalian genomic analysis: a practical guide. Academic Press, pp 75-135).

Various types of SSR markers can be generated, and SSR profiles from resistant lines can be obtained by gel electrophoresis of the amplification products. Scoring of marker genotype is based on the size of the amplified fragment. An SSR service for maize is available to the public on a contractual basis by DNA Landmarks in Saint-Jean-sur-Richelieu, Quebec, Canada.

Various types of FLP markers can also be generated. Most commonly, amplification primers are used to generate fragment length polymorphisms. Such FLP markers are in many ways similar to SSR markers, except that the region amplified by the primers is not typically a highly repetitive region. Still, the amplified region, or amplicon, will have sufficient variability among germplasm, often due to insertions or deletions, such that the fragments generated by the amplification primers can be distinguished among polymorphic individuals, and such indels are known to occur frequently in maize (Bhattramakki et al. (2002). Plant Mol Biol 48, 539-547; Rafalski (2002b), supra).

SNP markers detect single base pair nucleotide substitutions. Of all the molecular marker types, SNPs are the most abundant, thus having the potential to provide the highest genetic map resolution (Bhattramakki et al. 2002 Plant Molecular Biology 48:539-547). SNPs can be assayed at an even higher level of throughput than SSRs, in a so-called 'ultra-high-throughput' fashion, as they do not require large amounts of DNA and automation of the assay may be straight-forward. SNPs also have the promise of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing and coded spheres. Such methods have been reviewed in: Gut (2001) Hum Mutat 17 pp, 475-492: Shi (2001) Clin Chem 47, pp. 164-172; Kwok (2000) Pharmacogenomics 1, pp. 95-100: Bhattramakki and Rafalski (2001) Discovery and application of single nucleotide polymorphism markers in plants. In: R, J Henry, Ed, Plant Genotyping: The DNA Fingerprinting of Plants, CABI Publishing, VVallingford. A wide range of commercially available technologies utilize these and other methods to interrogate SNPs including Masscode™. (Qiagen), Invader® (Third Wave Technologies), SnapShot® (Applied Biosystems), Taqman® (Applied Biosystems) and Beadarrays™ (Illumina).

A number of SNPs together within a sequence, or across linked sequences, can be used to describe a haplotype for any particular genotype (Ching et al. (2002), BMC Genet. 3:19 pp Gupta et al. 2001, Rafalski (2002b), Plant Science 162:329-333). Haplotypes can be more informative than, single SNPs and can be more descriptive of any particular genotype. For example, single SNP may be allele 'T' for a specific line or variety with increased MRCV tolerance, but the allele 'T' might also occur in the maize breeding population being utilized for recurrent parents. In this case, a haplotype, e.g. a combination of alleles at linked SNP markers, may be more informative. Once a unique haplotype has been assigned to a donor chromosomal region, that haplotype can be used in that population or any subset thereof to determine whether an individual has a particular gene. See, for example, WO2003054229. Using automated high throughput marker detection platforms known to those of ordinary skill in the art makes this process highly efficient and effective.

The sequences listed in Table 3 can be readily used to obtain additional polymorphic SNPs (and other markers) within the QTL intervals listed in this disclosure. Markers within the described map regions can be hybridized to BACs or other genomic libraries, or electronically aligned with genome sequences, to find new sequences in the same approximate location as the described markers.

In addition to SSRs, FLPs and SNPs, as described above, other types of molecular markers are also widely used, including but not limited to markers developed from expressed sequence tags (ESTs), randomly amplified polymorphic DNA (RAPD), and other nucleic acid based markers.

Isozyme profiles and linked morphological characteristics can, in some cases, also be indirectly used as markers. Even though they do not directly detect DNA differences, they are often influenced by specific genetic differences. However, markers that detect DNA variation are far more numerous and polymorphic than isozyme or morphological markers (Tanksley (1983) Plant Molecular Biology Reporter 1:3-8).

Sequence alignments or contigs may also be used to find sequences upstream or downstream of the specific markers listed herein. These new sequences, close to the markers described herein, are then used to discover and develop functionally equivalent markers. For example, different physical and/or genetic maps are aligned to locate equivalent markers not described within this disclosure but that are within similar regions. These maps may be within the maize species, or even across other species that have been genetically or physically aligned with maize, such as rice, wheat, barley or sorghum.

In general, MAS uses polymorphic markers that have been identified as having a significant likelihood of co-segregation with MRCV resistance. Such markers are presumed to map near a gene or genes that give the plant its MRCV resistance phenotype, and are considered indicators for the desired trait, or markers. Plants are tested for the presence of a desired allele in the marker, and plants containing a desired genotype at one or more loci are expected to transfer the desired genotype, along with a desired phenotype, to their progeny. The means to identify maize plants that have increased MRCV resistance by identifying plants that have a specified allele at any one of marker loci described herein, including PZD00030.2, PZA02194-1, PZE-104104856, Mo17-14216, DAS-PZ-19059, PZE-104109680, PZE-104110452, PZB01461.2, DAS-PZ-4588, MAGI_38007, DAS-PZ-12232, MAGI_75461, PZA02614.2, chr4_206864219, KG-2634304, DAS-PZ-9024, DAS-PZ-11829, PZE-104135467, PZE-104136149, MAGI_73697, PZE-104137851, DAS-PZ-236, DAS-PZ-7082, MAGI_35446, DAS-PZ-12609, DAS-PZ-7622, DAS-PZ-8199, Mo17-11151, PZB02059.2, PZE-105084059, DAS-PZ-20613, PZA01608-1, DAS-PZ-10982, PZE-105106594, DAS-PZ-15377, and MAGI_105022-2, PZE-105159825, PZE-105160788, PZA00545.26, PZA02015-11, PZA03167.5, PZE-105166278, and PZE-105169090 are presented herein.

The interval presented herein finds use in MAS to select plants that demonstrate increased MRCV resistance. Any marker that maps within the chromosome 4 interval defined by and including PZD00030.2 and DAS-PZ-7622, within the chromosome 5 interval defined by and including DAS-PZ-8199 and MAGI_105022-2, and within the chromosome 5 interval defined by and including PZE-105159825 and PZE-105169090 can be used for this purpose. In addition, haplotypes comprising alleles at one or more marker loci within the chromosome 4 interval defined by and including PZD00030.2 and DAS-PZ-7622, within the chromosome 5 interval defined by and including DAS-PZ-8199 and MAGI_105022-2, and within the chromosome 5 interval defined by and including PZE-105159825 and PZE-105169090 can be used to introduce increased MRCV resistance into maize lines or varieties. Any allele or haplotype that is in linkage disequilibrium with an allele associated with increased MRCV resistance can be used in MAS to select plants with increased MRCV resistance.

EXAMPLES

The following examples are offered to illustrate, but not to limit, the appended claims. It is understood that the examples and embodiments described herein are for illustrative purposes only and that persons skilled in the art will recognize various reagents or parameters that can be altered without departing from the spirit of the invention or the scope of the appended claims.

Example 1: Plant Material

Two Dow AgroSciences (DAS) elite lines consistently display high levels of Mal de Rio Cuarto Virus (MRCV) resistance under infestation conditions. To identify QTL associated with each of these lines that display a high correlation to MRCV resistance, doubled haploid (DH) mapping populations were developed and phenotypically evaluated in two endemic regions known to have high levels of viral outbreaks. QTL mapping analyses were completed using data collected over two successive years from two different DH populations (Table 1).

TABLE 1

Population size and SNP marker counts for two DH populations evaluated for resistance to MRCV disease over two successive years.

| Populations | Year | Sample Size | Count |
|---|---|---|---|
| DH Population 1 | 2010 | 67 | 467 |
| DH Population 1 | 2011 | 112 | 417 |
| DH Population 2 | 2010 | 78 | 454 |
| DH Population 2 | 2011 | 110 | 405 |

Example 2: MRCV Disease Phenotype Evaluation

The DH mapping populations were evaluated for MRCV symptomology in two endemic environments, Sampacho and Suco, Argentina. Two replicate sample populations were designed as randomized complete block studies (RCB). Plots were arranged in either two 3 meter (m) rows, or one 6 m row, with nearly 25 plants per DH line. In 2010, populations were planted on two separate dates to increase the chance of matching the stage of highest susceptibility of the corn plants with the highest peak of the vector population. In 2011, all populations were planted on three different planting dates spaced approximately one week apart for the same reason. Herbicide and fungicide treatments were used as needed for preventive control. In 2010, disease symptoms were evaluated at 20 days after flowering. In 2011, MRCV symptomology was assessed at three different time points over the course of the season in an effort to capture the timeframe that most accurately demonstrated a variable range of disease incidence. The intention was to capture phenotype data before disease pressure reached saturation. In both years, disease ratings were characterized using a percent incidence and a severity scale (MDG, Mean Disease Grade) as follows:

$$MDG = \Sigma_{i=0}^{5} fi \cdot xi$$

where fi: frequency of grade i, and xi: value of i-th grade. Grades are shown in Table 2.

TABLE 2

Descriptions of the Mean Disease Grade of MRCV.

| Grade | Symptoms |
|---|---|
| 0 | healthy plants; no symptoms |
| 1 | slight symptoms in upper leaves and tassels |
| 2 | moderate symptoms, slight height reduction, shortening of upper internodes and ear |
| 3 | stronger height reduction, multiple and conical ears, plant still productive but reduced yield |
| 4 | plant height severely reduced, multiple ears, scarce or null grain production due to ear reduction and malformations |
| 5 | dead plants; if still alive, extreme dwarfism, absence of ears, upper leaves and tassel |

Example 3: DNA Extraction and Single Nucleotide Polymorphic (SNP) Analysis

JoinMap® 3.0 (Van Ooijen et al., 2001) was used to develop linkage maps for subsequent QTL analysis. Interval mapping and composite interval mapping was conducted using MapQTL® 5.0 (Van Ooijen et al., 2002). A permutation test consisting of 1000 iterations was completed to determine the significant logarithm-of-odds (LOD) threshold value using a genome-wide p value of 0.05. Loci with LOD scores greater than the calculated significant threshold were identified as potential QTL. The position with the largest LOD value on the linkage group was used as the estimated position of the QTL on the map.

A QTL was identified on chromosome 4 in DH mapping population 1 for both the Sampacho and Suco environments. The QTL was detected using the averaged 2011 phenotypic data from Sampacho and explained 30.5% of the variation for that environment. The QTL was also detected using the averaged 2011 phenotypic data from Suco and explained 38.6% of the variation in that environment. The chromosome 4 QTL is defined by the interval of PZD00030.2 and DAS-PZ-7622, with the QTL peak defining the subinterval of DAS-PZ-4588 and MAGI_75461 (Table 3).

Two QTLs were identified on chromosome 5 in DH mapping population 2. The first QTL was detected using the averaged 2011 Suco phenotypic data from each collection date and explained 12.3% of the variation at the first collection time point, 20.3% of the variation at the second time point and 16.5% of the variation at the third time point. This QTL was also detected in the Sampacho environment, but was not statistically significant. This first chromosome 5 QTL is defined by the interval of DAS-PZ-8199 and MAGI_105022-2, with the QTL peak defining the subinterval of PZB02059.2 and PZA01608-1 (Table 3).

The second QTL identified on chromosome 5 was detected using the 2011 Sampacho phenotypic data and was not detected with the Suco data. This QTL explains 18.3% of the variation and is defined by the interval of PZE-105159825 and PZE-105169090, with the QTL peak defining the subinterval of PZA02015-11 and PZE-105166278 (Table 3).

Example 4: Marker Framework and Use for Marker Assisted Selection

A set of common markers can be used to establish a framework for identifying markers in the QTL interval. Table 3 shows markers that are in consistent position relative to one another on the DAS internally derived map and the B73 reference genome, version 2. Physical locations of the DAS proprietary markers were determined using GBrowse, an open source web-application developed by the Generic Model Organism Database, to visualize annotated genomes (Stein et al. 2002). GBrowse links DAS proprietary marker and genomic map information with the publicly available B73 reference genome, version 2.

Closely linked markers flanking the locus of interest that have alleles in linkage disequilibrium with a favorable allele at that locus may be effectively used to select for progeny plants with increased MRCV resistance. Thus, the markers described herein, such as those listed in Table 3, as well as other markers genetically or physically mapped to the same chromosomal segments, may be used to select for maize plants with increased MRCV resistance. Typically, a set of these markers will be used (e.g. 2 or more, 3 or more, 4 or more, 5 or more) in the regions flanking the loci of interest. Optionally, a marker within the actual gene and/or locus may be used.

TABLE 3

Chromosome intervals and markers associated with MRCV resistance.

| QTL | Chr | Marker | SEQ ID NO. | SNP | Donor Allele | Physical Position (bp) |
|---|---|---|---|---|---|---|
| 1 | 4 | PZD00030.2 | 1 | A/G | G | 178889832 |
|  | 4 | PZA02194-1 | 2 | A/G | G | 181223123 |
|  | 4 | PZE-104104856 | 3 | T/C | T | 181227158 |
|  | 4 | Mo17-14216 | 4 | T/G | T | 181338456 |
|  | 4 | DAS-PZ-19059 | 5 | G/A | G | 185530452 |
|  | 4 | PZE-104109680 | 6 | T/C | C | 185868315 |
|  | 4 | PZE-104110452 | 7 | A/C | A | 186658864 |
|  | 4 | PZB01461.2 | 8 | A/T | A | 188385496 |
|  | 4 | DAS-PZ-4588 | 9 | C/A | A | 190008850 |
|  | 4 | MAGI_38007 | 10 | T/C | T | NA |
|  | 4 | DAS-PZ-12232 | 11 | G/A | G | 196822606 |
|  | 4 | MAGI_75461 | 12 | T/C | T | 199278901 |
|  | 4 | PZA02614.2 | 13 | A/G | G | 200539236 |
|  | 4 | chr4_206864219 | 14 | A/G | A | 203118823 |
|  | 4 | KG-2634304 | 15 | A/T | A | 207264493 |
|  | 4 | DAS-PZ-9024 | 16 | A/G | A | 219707115 |
|  | 4 | DAS-PZ-11829 | 17 | G/T | G | 220086621 |
|  | 4 | PZE-104135467 | 18 | T/G | G | 220654740 |
|  | 4 | PZE-104136149 | 19 | T/C | C | 221761481 |
|  | 4 | MAGI_73697 | 20 | T/G | G | 223875116 |
|  | 4 | PZE-104137851 | 21 | A/G | G | 224880981 |
|  | 4 | DAS-PZ-236 | 22 | G/A | G | 229340991 |
|  | 4 | DAS-PZ-7082 | 23 | T/C | T | 230482813 |
|  | 4 | MAGI_35446 | 24 | T/C | T | 231411365 |
|  | 4 | DAS-PZ-12609 | 25 | G/A | G | 234358607 |
|  | 4 | DAS-PZ-7622 | 26 | G/A | G | 234917252 |
| 2 | 5 | PZE-105159825 | 27 | C/G | C | 206893642 |
|  | 5 | PZE-105160788 | 28 | T/C | C | 207514452 |
|  | 5 | PZA00545.26 | 29 | C/G | G | 207708797 |
|  | 5 | PZA02015-11 | 30 | T/C | T | 208270391 |
|  | 5 | PZA03167.5 | 31 | T/C | C | 208350248 |
|  | 5 | PZE-105166278 | 32 | A/G | G | 209867293 |
|  | 5 | PZE-105169090 | 33 | A/G | G | 211073713 |
| 3 | 5 | DAS-PZ-8199 | 34 | T/A | T | 87109462 |
|  | 5 | Mo17-11151 | 35 | A/G | A | 88257368 |
|  | 5 | PZB02059.2 | 36 | A/G | G | 93237620 |
|  | 5 | PZE-105084059 | 37 | T/C | C | 101410478 |
|  | 5 | DAS-PZ-20613 | 38 | A/G | A | 155810701 |
|  | 5 | PZA01608-1 | 39 | T/C | C | 159288407 |
|  | 5 | DAS-PZ-10982 | 40 | A/C | A | 159912698 |
|  | 5 | PZE-105106594 | 41 | C/A | A | 162835750 |
|  | 5 | DAS-PZ-15377 | 42 | G/C | G | 163742654 |
|  | 5 | MAGI_105022-2 | 43 | C/G | C | 166397523 |

Physical positions were determined from the B73 reference genome, version 2.

REFERENCES

Di Renzo, M. A., Bonamico, N. C., Diaz, D. D., Ibanez, M. A., Faricell, M. E., Balzarini M. G. and Salerno, S. J. (2004). Microsatellite markers linked to QTL for resistance to Mal de Rio Cuarto disease in Zea mays L. J Agric Sci, 142:289-295.

Kreff, E. D., Pacheco, M. G., Diaz, D. G., Robredo, C. G., Puecher, D., Celiz, A., and Salerno, J. C. (2006). Resistance to Mal de Rio Cuarto Virus in maize: A QTL analysis. J Basic Appl Genet 17:41-50.

Martin, T., Franchino, J. A., Kreff, E. D., Procopiuk, A. M., Tomas, A., Luck, S. D., Shu, G. G. (2009). Major QTLs conferring resistance of corn to Fijivirus. WO 2009/058335.

What is claimed is:

1. A method for producing a Mal De Rio Cuarto Virus (MRCV)-resistant maize plant, the method comprising: crossing a first parental maize plant to a second parental maize plant, wherein the first parental maize plant comprises at least one single nucleotide polymorphism (SNP) genetic marker allele associated with MRCV resistance, wherein the marker allele is selected from the group consisting of A nucleotide at the SNP defined by SEQ ID NO:9 on maize chromosome 4, a T nucleotide at the SNP defined by SEQ ID NO:10 on maize chromosome 4, a G nucleotide at the SNP defined by SEQ ID NO:11 on maize chromosome 4, a T nucleotide at the SNP defined by SEQ ID NO:12 on maize chromosome 4, thereby producing at least one progeny maize plant;

screening nucleic acid molecules from the progeny maize plant(s) for the marker allele associated with MRCV resistance; and selecting a progeny plant that comprises the marker allele associated with MRCV resistance.

2. The method of claim 1, wherein the first parental maize plant or the second parental maize plant belongs to the Non-Stiff Stalk heterotic group.

3. The method according to claim 1, wherein the first parental maize plant comprises the marker alleles associated with MRCV resistance of an A nucleotide at the SNP defined by SEQ ID NO:9 on maize chromosome 4, a T nucleotide at the SNP defined by SEQ ID NO:10 on maize chromosome 4, a G nucleotide at the SNP defined by SEQ ID NO:11 on maize chromosome 4, and a T nucleotide at the SNP defined by SEQ ID NO:12 on maize chromosome 4, wherein screening the nucleic acid molecules from the progeny maize plant(s) comprises screening for at least one of marker the alleles associated with MRCV resistance comprised in the first parental plant; and wherein selecting the progeny plant comprises selecting a plant comprising the screened marker alleles associated with MRCV resistance comprised in the first parental plant.

4. The method according to claim 1, wherein the second parental maize plant is a maize plant from a maize variety comprising a gene or trait of interest, the method further comprising:

crossing the selected progeny plant with a plant from the maize variety comprising the gene or trait of interest, thereby producing at least one further progeny plant;

screening nucleic acid molecules from the further progeny maize plant(s) for the marker allele associated with MRCV resistance; and selecting a further progeny plant that comprises the marker allele associated with MRCV resistance, and the gene or trait of interest.

5. The method according to claim 3, wherein the second parental maize plant is a maize plant from a maize variety comprising a gene or trait of interest, the method further comprising:

crossing the selected progeny plant with a plant from the maize variety comprising the gene or trait of interest, thereby producing at least one further progeny plant;

screening nucleic acid molecules from the further progeny maize plant(s) for the more than one of the plurality of marker alleles associated with MRCV resistance; and selecting a further progeny plant that comprises the more than one of the plurality of marker alleles associated with MRCV resistance, and the gene or trait of interest.

* * * * *

SEQUENCE LISTING

<160> NUMBER OF SEQ ID NOS: 43

<210> SEQ ID NO 1
<211> LENGTH: 121
<212> TYPE: DNA
<213> ORGANISM: Zea mays

<400> SEQUENCE: 1

```
ctcattcata tgggcaagca atgttttgtt ttaaacacat ttcccgtgat aagtactaac      60
rtttgagtag cgggaaggta cacttctttt aatttacatt aaaaaatgtt tgcaaactta     120
c                                                                     121
```

<210> SEQ ID NO 2
<211> LENGTH: 121
<212> TYPE: DNA
<213> ORGANISM: Zea mays

<400> SEQUENCE: 2

```
agatgtcata atgcaccaga tgtttcacaa agcatgctga aaagctttgt gctgacataa      60
rcctaatcac acattgtcat atccttcatc aaaactttgt cacatccttc atcaaaacat     120
t                                                                     121
```

<210> SEQ ID NO 3
<211> LENGTH: 101
<212> TYPE: DNA
<213> ORGANISM: Zea mays

<400> SEQUENCE: 3

```
gatgggagaa attagcatcg aactaactcc cgtccaaacc aaacggcaag ytactgttac      60
cggtattccc gggtatcgac gttgggtctc ccgggagaat c                         101
```

<210> SEQ ID NO 4
<211> LENGTH: 121
<212> TYPE: DNA
<213> ORGANISM: Zea mays

<400> SEQUENCE: 4

```
ccacgaccgg gtccacctcg ccagtcaccg tcaccgtcac cgtcaccttc tgctgcagcc      60
kgttcacctc cacatgctgc actcctgcac aggggcgaat ctaggggtt atcggggtca     120 g                                                                     121
```

<210> SEQ ID NO 5
<211> LENGTH: 201
<212> TYPE: DNA
<213> ORGANISM: Zea mays

<400> SEQUENCE: 5

```
gcaatgttcc gactagtttc taacccatgt acaaattaag ggcagtactt aaaaaatgtt      60
ttctacacgt atccaatcta ccaatactgt gaccatttta ractaattcg aattctgtcc     120
aaatcctagg tacattagcc aatggtaaaa acaagcaaa gaatatgaga ataccgttg      180 ccctaatgct gggagaaggg g                                              201
```

<210> SEQ ID NO 6
<211> LENGTH: 101
<212> TYPE: DNA
<213> ORGANISM: Zea mays

<400> SEQUENCE: 6
tcatccacag tgatttgtgc ggccccatga caccagcgac tccaggcaag ygatgctact     60
tcttgctcct agtggacgat acctcctgat tcatgtgggc a                         101

<210> SEQ ID NO 7
<211> LENGTH: 101
<212> TYPE: DNA
<213> ORGANISM: Zea mays

<400> SEQUENCE: 7
gaaggtgtgg gtacggtctg tgcatgatga atcatgagtc gagcgctttt mcagggttc      60 gaggctgcca tcgcagccgg cgcgaaggaa atcgcggtct t                         101

<210> SEQ ID NO 8
<211> LENGTH: 121
<212> TYPE: DNA
<213> ORGANISM: Zea mays
<220> FEATURE:
<221> NAME/KEY: misc_feature
<222> LOCATION: (6)..(8)
<223> OTHER INFORMATION: n is A, T, G, or C
<220> FEATURE:
<221> NAME/KEY: misc_feature
<222> LOCATION: (23)..(23)
<223> OTHER INFORMATION: n is A, T, G, or C

<400> SEQUENCE: 8
attagnnnca ggcatttwtt ttncaggag agaagtcgta agctatgaga gcccgagacc      60
wggcattggt atccacaggt tcatctttgt tctcttcaag caraagcgca ggcagcagca    120 r                                                                    121

<210> SEQ ID NO 9
<211> LENGTH: 201
<212> TYPE: DNA
<213> ORGANISM: Zea mays

<400> SEQUENCE: 9
gatgttgttg cttctttaac cgcggcatcg gtatgtgatc gccggcgtgg ttcactgcct     60
attattgttg ctggcaatgg tttttagctg taacaatgct mtgtttaaat ggagaatgtc    120
atctttcgat ggttgtttct agaaacaaga ataggctgag ttgtgagtac aaatagcctc    180
caagggtgat cctcactcag c                                              201

<210> SEQ ID NO 10
<211> LENGTH: 121
<212> TYPE: DNA
<213> ORGANISM: Zea mays

<400> SEQUENCE: 10
atgttgtaca cccgaataac ctggtggttt agatttggat cgtcctgagt tcaattgtat     60
yctggggatc aatattggtt ttccctccct aattattgaa cttgacatgt gcacggtgta    120
g                                                                    121

<210> SEQ ID NO 11
<211> LENGTH: 201
<212> TYPE: DNA
<213> ORGANISM: Zea mays

<400> SEQUENCE: 11
actagctagc attatatatc ttttagaccg ggacaacatg tgaaggtgag ttgttcagcc     60

```
agagtttcca taattaaagt tactcagcat gttgtcacca rcatcaaaga gtgcgttgca      120
agcatccatc gtcgatccat gatgtgttaa tttattgtac acacaaacac taagaaaaaa      180
ataattaatt tgccggcagc c                                                201

<210> SEQ ID NO 12
<211> LENGTH: 121
<212> TYPE: DNA
<213> ORGANISM: Zea mays

<400> SEQUENCE: 12
tccatgaact cgtctgttgc gtctatgtac acctccatgg tttgaactcg tcggggactt      60
ygctcgatgt gttattaatc tcatgctcat ccttccgcta atgttgcctg gcggcatcgc      120
c                                                                      121

<210> SEQ ID NO 13
<211> LENGTH: 108
<212> TYPE: DNA
<213> ORGANISM: Zea mays

<400> SEQUENCE: 13
tacgatgggc ccacatcatc ccatagtggt agggattaag cagcagggcc atctcttctt      60
rgacttcctc gctcgccttg actccttgct gttgctgaaa ccgttctg                   108

<210> SEQ ID NO 14
<211> LENGTH: 501
<212> TYPE: DNA
<213> ORGANISM: Zea mays

<400> SEQUENCE: 14
cgatagtcct ggtactaaat ctgaatttaa aaagcctaat atgtcaaagg ttaaggaaga      60
cgtatcatcg tgcaatacta attcacagcc gagaagccca ctcggattat caatttggca      120
caacaagagg ctaggaaaac tcggtgcaca aaagttgaag aagagaggca tgctatgggt      180
ccctaatggg aggtctcaat atcaaggtaa ggatgaggct ttaggaagag gtgaagtgaa      240
ggcaaacata rggaagaaat caagtacaag atgtatgggt gaaaggtttg ccccaactta      300
tcaaagctat cggtctttgc atcgtccata attttagtt gtgtcgtata cgtcgtccca       360
aggtatgttc ggttgttggg daccttcggc gtccgaaggt cctcaaaaac aggatttaac      420
agtattcctg cagtacaatg tgtaaacagg taccctcgga ctaaagtcgg cattgcagtg      480
gaccggaata atacgaaggt t                                                501

<210> SEQ ID NO 15
<211> LENGTH: 81
<212> TYPE: DNA
<213> ORGANISM: Zea mays

<400> SEQUENCE: 15
accgaatggc aaccatgtag tagtgcttca tgaaacatgt wtgtgcactg agttcccact      60
gcacaagatg tgtgccaata a                                                81

<210> SEQ ID NO 16
<211> LENGTH: 201
<212> TYPE: DNA
<213> ORGANISM: Zea mays

<400> SEQUENCE: 16
agtacatggg aacctcggaa aggccgtgcc cggtgccagg attccagaat tcaccgggag      60
```

```
aatgattctt gtagtgatag tccaaggtca tcagtgtcag ratctcatag aagtgactcc    120
agcactgaag aacccacgag cagtaaatcg catcgccacc ttcaaaaggt caagaagggt    180
ttgggcaagc tagctggagc a                                              201
```

<210> SEQ ID NO 17
<211> LENGTH: 201
<212> TYPE: DNA
<213> ORGANISM: Zea mays

<400> SEQUENCE: 17

```
gctgccggac gagcaagcgc cacgcgcgcg ccgtgcctgc catgagccgt cagtccgcag     60
tccgcagtcc gcagccacac ttttgctaaa ccctagtaaa katacgatac gaagcgcaaa    120
cgcttgcctc atcctcgaat tcgccatggc gatgcccacc acctcgtctg cttccccatg    180
ccaggcaccg tcgcccgccg g                                              201
```

<210> SEQ ID NO 18
<211> LENGTH: 101
<212> TYPE: DNA
<213> ORGANISM: Zea mays

<400> SEQUENCE: 18

```
gtaccggaat ttgcagcaaa tttatctttc tgtacccctg ttacagctga kgtcacagca     60
gaaccaaact ggccacccat tgaactgcct gataactctc c                        101
```

<210> SEQ ID NO 19
<211> LENGTH: 101
<212> TYPE: DNA
<213> ORGANISM: Zea mays

<400> SEQUENCE: 19

```
gagctcgagg ttggtgttgg agaaaccgtt gtaggcgaac atgggatcgt yacttcttgc     60
gaacgaggtt gcaaaggtga ggccaagaaa caccaccagc t                        101
```

<210> SEQ ID NO 20
<211> LENGTH: 121
<212> TYPE: DNA
<213> ORGANISM: Zea mays

<400> SEQUENCE: 20

```
tttggaggtt gatgttgtca tcttttaact aaggtcattt ctatcatcct gaattcaaga     60
kattattgag aaaatcttcc aatttgtgtg gctgggtctc tgttgttcga tgcatgttaa    120
c                                                                    121
```

<210> SEQ ID NO 21
<211> LENGTH: 101
<212> TYPE: DNA
<213> ORGANISM: Zea mays

<400> SEQUENCE: 21

```
gccacgctga tgagcacgac gaggacagcg acgacgagga ggatgagcaa rtggaagaga     60
tggtccggcg gttcaggaag gcgatcatga ggaggagatt c                        101
```

<210> SEQ ID NO 22
<211> LENGTH: 201
<212> TYPE: DNA
<213> ORGANISM: Zea mays

<400> SEQUENCE: 22
tgcgcgtacc accgaaaact aactacaaac tgagcccaca aagcctggcc atggccattt     60
caatggctcg ggcatttgtt gcccccaagg aaatagatac rccctagtgc tcgcttctag    120
ttgtacaggg agcatgccgg agtgaaggat ccaaaaggcg accgtagggg ggtgatgtga    180
ttgagagagc caattaaatt c                                              201

<210> SEQ ID NO 23
<211> LENGTH: 201
<212> TYPE: DNA
<213> ORGANISM: Zea mays

<400> SEQUENCE: 23
acgagatcct gcacaggatt actttttgctg tcagtttgag aagccccaaa ctgacgagcg     60
taccaagcca cttcgtctgc cctataacac aggtaactcg ygtgcggcat ctgaatcggt    120
ttcggctctc cttcgcttgt gctttaccag aacggaaccc gcgtgcagga gctgatggag    180
gatcctcacg tcgccgcaga c                                              201

<210> SEQ ID NO 24
<211> LENGTH: 121
<212> TYPE: DNA
<213> ORGANISM: Zea mays

<400> SEQUENCE: 24
attcaacttt gaaaaaaaaa aacaagccat agcaaatgtg cactgtgcag ccattcattc     60
yctgatcctt acacaacatt ttcccgtttc tagttacagt acagttctat tatacatggc    120
a                                                                    121

<210> SEQ ID NO 25
<211> LENGTH: 201
<212> TYPE: DNA
<213> ORGANISM: Zea mays

<400> SEQUENCE: 25
atgagctgaa atactatatc acaggtctat tgtcattttt atcacacact gctgtattta     60
gatgaataat acacaagcat ttgaggattc aaatagacca rtcctgtgca aatgttcgta    120
ctctgagata ttagcaccag agtgtaacat ctgagaccaa cgcaactcca ggccatcttc    180
tcagctgaaa ggatgtagga a                                              201

<210> SEQ ID NO 26
<211> LENGTH: 201
<212> TYPE: DNA
<213> ORGANISM: Zea mays

<400> SEQUENCE: 26
cccaagctct gctcaagccg atcgagcgag gctaaggccc agatcctacg atggcgatca     60
ccgtgggaat tgccgacgcc ccttacatcc tcgtgggccc rcccgaggct cgccagagcc    120
actccgccgc cctggccact ggggccgcgc tagcgccgac gcgggaggag ttcccagacc    180
tgacggacgc gttctccaac g                                              201

<210> SEQ ID NO 27
<211> LENGTH: 101
<212> TYPE: DNA
<213> ORGANISM: Zea mays

<400> SEQUENCE: 27

```
gccagtgcta gagcgagaga agctgagacc tggacgttgt cgatgagttt stccagactc    60
ttcagcttcc ggtatggcca gcgcgtgacg ccaagcttcc t                       101

<210> SEQ ID NO 28
<211> LENGTH: 101
<212> TYPE: DNA
<213> ORGANISM: Zea mays

<400> SEQUENCE: 28
cggtcacaaa atcaaccgta tttaggccac cttgcagctt ggatagttgc ycttgcatgt    60
agtctaaaga ttctatgaag gttctggata cagcaggtcc a                      101

<210> SEQ ID NO 29
<211> LENGTH: 121
<212> TYPE: DNA
<213> ORGANISM: Zea mays

<400> SEQUENCE: 29
gaaaacagag cagcaccaca gatgcataca atgtgagatc tgttgtgacs ttacctcctt    60
sgcttccttt tttggaatgc cttcccgcat tgccacaagc ttytcgacaa cctcaggcta   120
a                                                                   121

<210> SEQ ID NO 30
<211> LENGTH: 121
<212> TYPE: DNA
<213> ORGANISM: Zea mays

<400> SEQUENCE: 30
tctttggtac accacattgg agacacatcc taaacamtga gccgaagtca caattaagaa    60
yrctaatagt attaaggaat tctggtatat attagagttc acgtaaaaca tgtacacaag   120
c                                                                   121

<210> SEQ ID NO 31
<211> LENGTH: 121
<212> TYPE: DNA
<213> ORGANISM: Zea mays
<220> FEATURE:
<221> NAME/KEY: misc_feature
<222> LOCATION: (5)..(5)
<223> OTHER INFORMATION: n is A, T, G, or C

<400> SEQUENCE: 31
ttganytcrt tatcagtccg cccagggagg tgctttgcga tagctgacca tctggtttga    60
ycatrrcaac agttgacact ggattagcat agcatgcact acgtacaagt maaaaatacg   120
a                                                                   121

<210> SEQ ID NO 32
<211> LENGTH: 101
<212> TYPE: DNA
<213> ORGANISM: Zea mays

<400> SEQUENCE: 32
cgacgacgag ttcggccaga gcagcgctga gagctacggc aacatgctgc rgaacaaggc    60
tttcggtggt ggtacggacc gatctttggt tggcaacaga c                      101

<210> SEQ ID NO 33
<211> LENGTH: 101
<212> TYPE: DNA
```

<213> ORGANISM: Zea mays

<400> SEQUENCE: 33

| taccacgagg tgtctagcta cagctagctc ctcctccgag gcgctacata rcctcgctgc | 60 |
| tacgcaggtg gtggtggtgg tggtagcgga gggaggtaca a | 101 |

<210> SEQ ID NO 34
<211> LENGTH: 201
<212> TYPE: DNA
<213> ORGANISM: Zea mays

<400> SEQUENCE: 34

| taggaataaa caagcgctcg tgggtacaag gctacaagct tatggaactt tcaaggcggc | 60 |
| aacaattagc ctctttgtgt gactgtgtcc tacggacggt wttttctgt ttaaaaccgg | 120 |
| ttcttgagtt gcttttatta taaaataatt atctactcag agacgttgag ttgtaatagc | 180 |
| ttatccgatt ttctattcaa a | 201 |

<210> SEQ ID NO 35
<211> LENGTH: 121
<212> TYPE: DNA
<213> ORGANISM: Zea mays

<400> SEQUENCE: 35

| gcaccaaagt tccagtacaa cgggcaactc acttgaaact tccatagttc cagaattcct | 60 |
| rcactgcatg tcatatcgga atccaatggc tgtaaagcag acgaatgccg ttgcatgtgt | 120 |
| g | 121 |

<210> SEQ ID NO 36
<211> LENGTH: 121
<212> TYPE: DNA
<213> ORGANISM: Zea mays

<400> SEQUENCE: 36

| gcaggaccgc gcaracratg gcgtcycctt cattgatggg gactgggaac tggtctagca | 60 |
| rgtttcagtt ctctacatca agtctgcctt cgtgtgarat tttccgcatt tgtggttgtg | 120 |
| g | 121 |

<210> SEQ ID NO 37
<211> LENGTH: 101
<212> TYPE: DNA
<213> ORGANISM: Zea mays

<400> SEQUENCE: 37

| aatcgtgcgc cgccgctatt ggtgtggtcc gctgtcggcc acctctccgc ygcgttgtac | 60 |
| ttaggccatc accggtgaat tgctcattgc gtgtgccagt g | 101 |

<210> SEQ ID NO 38
<211> LENGTH: 201
<212> TYPE: DNA
<213> ORGANISM: Zea mays

<400> SEQUENCE: 38

| gatgtccgcc gaaaactact gtaagatgga agggtaatca tcaataagtg attcatgttt | 60 |
| gtacaacagg acctagccgg gctaatacat cgacatcgaa rcataaaaca gaaagaattg | 120 |
| aatccaagct ctgacaaaaa gaaacctaga gataaaaaca gagaaaatgg gtaggggta | 180 |
| ggggacgagt accgagaggc g | 201 |

```
<210> SEQ ID NO 39
<211> LENGTH: 121
<212> TYPE: DNA
<213> ORGANISM: Zea mays

<400> SEQUENCE: 39
tgatcgctga tcctgtctta ccagattgtg tcgagacaga aataagcata gatttctcac     60
ygtttgtctg ttattttctg gttagacatc caaagactac cttgagaaac agcagggcga    120
a                                                                    121

<210> SEQ ID NO 40
<211> LENGTH: 201
<212> TYPE: DNA
<213> ORGANISM: Zea mays

<400> SEQUENCE: 40
ggaataccgc cacgtgttcc cactgccgcc aaccgaggca gccccggcgg ccaccgttat     60
atataaccac gcgccaccac ccaacaacag cacagcaacc magtgatcaa ttcaagcaac    120
acaccgacga agcaagcaaa gccaagcgga agcggtcagc gtcagaatag tatggcggtg    180
tccgcggcca agatggccgt c                                              201

<210> SEQ ID NO 41
<211> LENGTH: 101
<212> TYPE: DNA
<213> ORGANISM: Zea mays

<400> SEQUENCE: 41
gcagagctag aattagtttc aaccagccga ctagctgagc tctgttgctg mtgtgaagca     60
gaagccacat cttgctgttc ctcattgcca tctgcgccgc t                        101

<210> SEQ ID NO 42
<211> LENGTH: 201
<212> TYPE: DNA
<213> ORGANISM: Zea mays

<400> SEQUENCE: 42
gtgagccgtg ctaccccttg gccgaggcta ctggcgattg cattggatct ttttcttgga     60
aacctgtggc tcggctctcg agctcttcct gtccacacaa sctctagcca attctatcca    120
acccatactt tcctgctccc tgcccatgct catcactcgt gccatctgcc ggccggcaac    180
tgcttatttg cacgtttgtt c                                              201

<210> SEQ ID NO 43
<211> LENGTH: 121
<212> TYPE: DNA
<213> ORGANISM: Zea mays

<400> SEQUENCE: 43
acagaaccaa atttgacaac aattaacagt atcctttatg tagcatcagg ttattcatta     60
stgtcaggtg ctagcaacaa cactgcactc agaaacagcc cacaaaggta tgccctaacc    120
c                                                                    121
```